(12) United States Patent
Reinecke et al.

(10) Patent No.: US 7,001,351 B2
(45) Date of Patent: Feb. 21, 2006

(54) BRACE WITH INTEGRATED LUMBAR SUPPORT SYSTEM

(75) Inventors: Steven M. Reinecke, Dallas, TX (US); Paul J. Vasta, Jr., McKinney, TX (US)

(73) Assignee: AMEI Technologies, Inc., Wilmington, DE (US)

( * ) Notice: Subject to any disclaimer, the term of this patent is extended or adjusted under 35 U.S.C. 154(b) by 0 days.

(21) Appl. No.: 10/713,880

(22) Filed: Nov. 13, 2003

(65) Prior Publication Data

US 2004/0097857 A1  May 20, 2004

Related U.S. Application Data

(63) Continuation-in-part of application No. 10/407,052, filed on Apr. 3, 2003.

(60) Provisional application No. 60/512,990, filed on Oct. 21, 2003, provisional application No. 60/419,809, filed on Oct. 17, 2002.

(51) Int. Cl.
  *A61F 5/00* (2006.01)

(52) U.S. Cl. ............................ 602/19; 602/5; 128/874; 128/876

(58) Field of Classification Search ................ 128/874, 128/845, 846, 876; 602/13, 19, 5
  See application file for complete search history.

(56) References Cited

U.S. PATENT DOCUMENTS

| | | | |
|---|---|---|---|
| 1,589,670 A | 6/1926 | Vartia | |
| 2,835,247 A | 5/1958 | Stabholc | 128/78 |
| 3,029,810 A | 8/1962 | Martin | 128/78 |
| 3,351,053 A | 11/1967 | Stuttle | 128/78 |
| 3,420,230 A | 1/1969 | Ballard | 128/75 |
| 3,521,623 A | 7/1970 | Nichols et al. | 128/78 |
| 3,548,817 A | 12/1970 | Mittasch | 128/75 |
| 3,598,114 A | 8/1971 | Lewis | 128/78 |
| 3,889,664 A | 6/1975 | Heuser et al. | 128/75 |
| 3,926,182 A | 12/1975 | Stabholz | 128/75 |
| 4,135,503 A | 1/1979 | Romano | 128/78 |
| 4,178,922 A * | 12/1979 | Curlee | 602/19 |
| 4,269,179 A | 5/1981 | Burton et al. | 128/75 |
| 4,497,517 A | 2/1985 | Gmeiner et al. | 297/231 |
| 4,552,135 A | 11/1985 | Racz et al. | 128/78 |
| 4,559,933 A | 12/1985 | Batard et al. | 128/78 |
| 4,599,998 A | 7/1986 | Castillo | 128/77 |
| 4,622,957 A | 11/1986 | Curlee | 128/78 |

(Continued)

FOREIGN PATENT DOCUMENTS

CH  0689797 A  11/1999

(Continued)

OTHER PUBLICATIONS

PCT, Notification of International Search Report or the Declaration and International Search Report, Jul. 30, 2004, 4 pages.

(Continued)

*Primary Examiner*—Henry Bennett
*Assistant Examiner*—Dinnatia Doster-Greene
(74) *Attorney, Agent, or Firm*—Baker & McKenzie (57) ABSTRACT

In one embodiment, a brace with an integrated lumbar support system includes a belt adapted to be positioned about a user's lower torso, the belt including a tube at least partially integrated within the belt. The brace includes a lumbar pad coupled to the belt, the lumbar pad adapted to be positioned proximate the user's lumbar region and to be inflated to provide lumbar support to the user. The brace includes a pump coupled to the belt, the pump adapted to provide air to the lumbar pad through the tube at least partially integrated within the belt to inflate the lumbar pad.

5 Claims, 8 Drawing Sheets

U.S. PATENT DOCUMENTS

| | | | |
|---|---|---|---|
| 4,682,587 A * | 7/1987 | Curlee | 602/13 |
| 4,682,588 A | 7/1987 | Curlee | 128/78 |
| 4,685,668 A | 8/1987 | Newlin, Jr. | 272/123 |
| 4,691,696 A | 9/1987 | Farfan de los Godos | 128/78 |
| 4,702,235 A | 10/1987 | Hong | 128/78 |
| 4,715,362 A | 12/1987 | Scott | 128/75 |
| 4,721,102 A | 1/1988 | Pethybridge | |
| 4,836,194 A | 6/1989 | Sebastian et al. | 128/78 |
| 4,884,562 A | 12/1989 | Stone | 128/78 |
| 4,898,185 A | 2/1990 | Fuller | 128/876 |
| 4,907,575 A | 3/1990 | Satterthwaite | 128/75 |
| 4,991,572 A | 2/1991 | Chases | 128/75 |
| 4,991,573 A | 2/1991 | Miller | 128/78 |
| 5,060,640 A | 10/1991 | Rasmusson | 128/80 C |
| 5,062,414 A | 11/1991 | Grim | 128/68.1 |
| 5,111,807 A | 5/1992 | Spahn et al. | 606/244 |
| 5,144,943 A | 9/1992 | Luttrell et al. | 128/25 B |
| 5,188,586 A | 2/1993 | Castel et al. | 602/19 |
| 5,195,948 A * | 3/1993 | Hill et al. | 602/19 |
| 5,207,635 A | 5/1993 | Richards et al. | 602/19 |
| 5,256,135 A | 10/1993 | Avihod | 602/19 |
| 5,363,863 A | 11/1994 | Lelli et al. | 128/876 |
| 5,382,226 A | 1/1995 | Graham | 602/32 |
| RE34,883 E * | 3/1995 | Grim | 602/13 |
| 5,403,266 A | 4/1995 | Bragg et al. | 602/5 |
| 5,437,615 A * | 8/1995 | Pekar et al. | 602/19 |
| 5,437,617 A | 8/1995 | Heinz et al. | 602/19 |
| 5,441,479 A | 8/1995 | Chitwood | 602/18 |
| 5,450,858 A * | 9/1995 | Zablotsky et al. | 128/876 |
| 5,462,518 A | 10/1995 | Hatley et al. | 602/36 |
| 5,586,969 A | 12/1996 | Yewer, Jr. | 602/19 |
| 5,681,267 A | 10/1997 | Molino et al. | 602/19 |
| 5,690,609 A | 11/1997 | Heinze, III | 602/19 |
| 5,695,452 A * | 12/1997 | Grim et al. | 602/6 |
| 5,722,940 A | 3/1998 | Gaylord, Jr. et al. | 602/19 |
| 5,913,410 A | 6/1999 | Tsuchiya | 2/311 |
| 5,916,188 A | 6/1999 | Ousdal | 602/32 |
| 5,950,628 A * | 9/1999 | Dunfee | 128/874 |
| 6,099,490 A | 8/2000 | Turtzo | 602/19 |
| 6,146,345 A | 11/2000 | Mignard | 602/19 |
| 6,331,170 B1 * | 12/2001 | Ordway | 602/19 |
| 6,364,186 B1 * | 4/2002 | Gilmour et al. | 224/637 |
| 6,533,740 B1 | 3/2003 | Reinecke et al. | |
| 2002/0193720 A1 | 12/2002 | Reinecke et al. | |
| 2003/0195446 A1 | 10/2003 | Reinecke et al. | |
| 2003/0208147 A1 | 11/2003 | Reinecke et al. | |
| 2004/0077982 A1 | 4/2004 | Reinecke et al. | |

FOREIGN PATENT DOCUMENTS

| | | |
|---|---|---|
| CH | 0690398 A | 8/2000 |
| DE | 10007634 A1 | 7/2001 |
| DE | 10007635 A1 | 7/2001 |
| WO | WO 02/069857 * | 9/2002 |

OTHER PUBLICATIONS

Reinecke et al., "Traction Device," U.S. Appl. No. 09/875,486, pending now issued as Pat No. 6,689,082 courtesy copy of P. 1 included.

Reinecke et al., "Canting Mechanism for an Ambulatory Support Device," U.S. Appl. No. 09/875,473, pending now issued as Pat No. 6,702,771 courtesy copy of P. 1 included.

Reinecke et al., "Traction Device Adjustment Mechanism and Method," U.S. Appl. No. 09/875,315, pending now issued as Pat No. 6,635,025 B1 courtesy copy of P. 1 included.

Reinecke, et al., "Traction Device and Associated Lifting Mechanisms," U.S. Appl. No. 10/335,694, pending now issued as Pat No. 6,776,767 B2 courtesy copy of P. 1 included.

PCT, Notification of Transmittal of the International Search Report or the Declaration, 6 pages PCT/US02/5179 corresponding to US 09/875,486 included.

PCT, Notification of Transmittal of the International Search Report or the Declaration, 6 pages PCT/US02/05334 corresponding to US 09/875,315 included.

PCT, Notification of Transmittal of the International Search Report or the Declaration, 7 pages PCT/US02/05180 corresponding to US 09/875,473 uncluded.

PCT, Notification of Transmittal of the International Search Report or the Declaration, 6 pages PCT/US02/05333 corresponding to US 09/875,332 and 10/335,694 included.

PCT, Notification of Transmittal of the International Search Report or the Declaration, 6 pages PCT/US02/18675 corresponding to US 10/154,695 included.

* cited by examiner

BRACE WITH INTEGRATED LUMBAR SUPPORT SYSTEM

RELATED APPLICATIONS

This application claims the benefit under 35 U.S.C. § 119(e) of U.S. Provisional Application No. 60/512,990 filed Oct. 21, 2003, entitled "Brace with Integrated Lumbar Support System." This application is a continuation-in-part of U.S. application Ser. No. 10/407,052 filed Apr. 3, 2003, entitled "Dynamically Adjustable Stabilization Brace," now pending, which claims the benefit under 35 U.S.C. § 119(e) of U.S. Provisional Application No. 60/419,809 filed Oct. 17, 2002, entitled "Dynamically Adjustable Stabilization Brace."

TECHNICAL FIELD OF THE INVENTION

This invention relates to the field of medical devices and, more particularly, to a brace with an integrated lumbar support system.

BACKGROUND

People have long dealt with the pain, aggravation, and loss of productivity arising from bodily injuries, such as those to the back, knees, and elbows. In fact most people will at some point in their lives be at least temporarily incapacitated by back pain, particularly low back pain. The relative ease with which injuries to the back and other portions of the body are incurred merely adds to the overall severity of the problem of dealing with bodily injuries. The forms of treatment vary over the length of time that a patient experiences pain. For example, eighty percent of low back pain sufferers heal over the course of six weeks with minimal intervention. However, the remaining twenty percent of sufferers create the greatest challenges and cost to the medical system. After the acute phase, surgical intervention or more invasive forms of treatment may be selected. However, minimally-invasive or non-invasive treatment methods are preferred. Another concern when dealing with bodily injuries is rehabilitation. Because injuries to the back, knees, elbows, and other portions of the body do not typically heal within a day or two, effective methods of rehabilitation are important for recovery.

SUMMARY OF THE INVENTION

According to the present invention, disadvantages and problems associated with previous techniques for rehabilitating injuries may be reduced or eliminated.

In one embodiment, a brace with an integrated lumbar support system includes a belt adapted to be positioned about a user's lower torso, the belt including a tube at least partially integrated within the belt. The brace includes a lumbar pad coupled to the belt, the lumbar pad adapted to be positioned proximate the user's lumbar region and to be inflated to provide lumbar support to the user. The brace includes a pump coupled to the belt, the pump adapted to provide air to the lumbar pad through the tube at least partially integrated within the belt to inflate the lumbar pad Certain embodiments of the present invention may provide one or more technical advantages. Certain embodiments of the invention may provide all, some, or none of these advantages. For example, certain embodiments provide a stabilization brace that allows a range of motion of the user's spine, while limiting the degree of flexion to a predetermined range, to improve healing and rehabilitation relative to techniques in which the spine is substantially immobilized using a brace or otherwise. Certain embodiments provide resistance against such flexion to stabilize the spine and limit bending, lifting, or other activities. In certain embodiments, the predetermined range of flexion, the resistance provided against such flexion, or both, may be adjusted according to particular needs. Such adjustability may improve the effectiveness of rehabilitation. Certain embodiments provide a stabilization brace including belts with canting mechanisms that allow the stabilization brace to be properly fitted for each particular user. Such canting mechanisms may rotate to allow the corresponding belts to conform to the underlying structure of the user's body, such as the natural conical shapes of the user's upper torso below the ribs and user's lower torso above the hips for example. The belts may be cut to appropriate lengths in properly fitting the stabilization brace to the user. Once a proper fit is achieved, the canting mechanisms may be locked into position to maintain the fit so that maximum comfort and effectiveness may be achieved. Stabilization braces in certain embodiments may be used in association with joints other than the spine, such as the knee, elbow, or neck for example. Certain embodiments provide a stabilization brace that is ambulatory, meaning that the brace is portable and wearable during the user's daily activities. The ambulatory nature of the stabilization brace provides more convenience to the user, causes less impact on the user's daily activities, and perhaps most importantly promotes healing and rehabilitation relative to previous techniques. Certain embodiments provide a brace with an integrated lumbar support system including an inflatable lumbar pad, a pump, and a tube at least partially integrated within a belt of the brace to transport air between the pump and the lumbar pad. Since the tube is at least partially integrated within the belt, the tube may be cut to an appropriate length as the belt is cut to length to fit the user. Certain embodiments may provide all, some, or none of these technical advantages. Certain embodiments may provide one or more other technical advantages, one or more of which may be readily apparent to those skilled in the art from the figures, description and claims included herein.

BRIEF DESCRIPTION OF THE DRAWINGS

To provide a more complete understanding of the present invention and certain features and advantages thereof, reference is made to the following description taken in conjunction with the accompanying drawings, in which.

DESCRIPTION OF EXAMPLE EMBODIMENTS

Figure 1A:
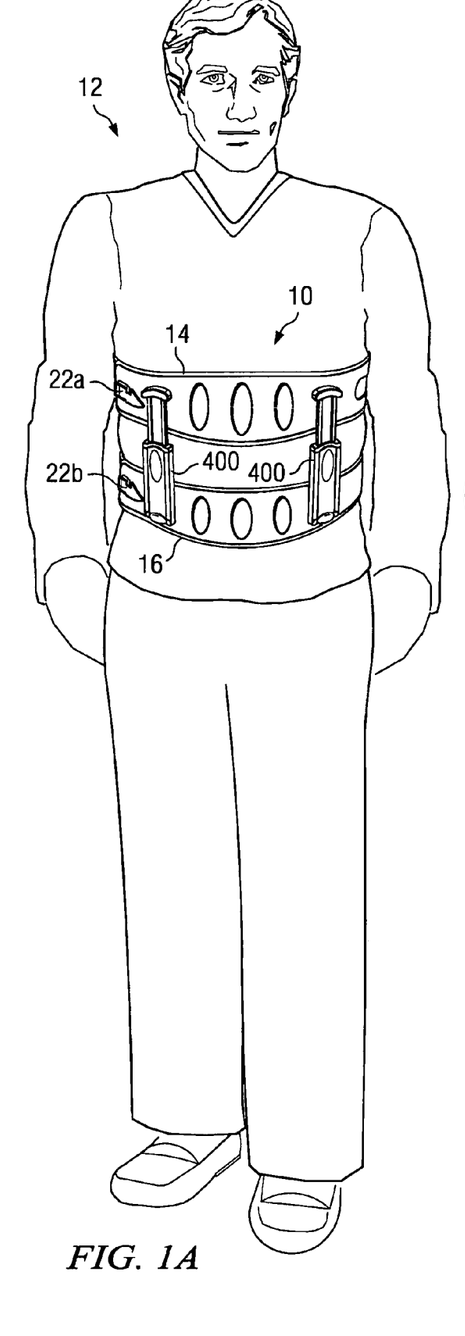
FIGS. 1A and 1B are front and rear views, respectively, illustrating a user wearing an example stabilization brace.
Figure 1B:
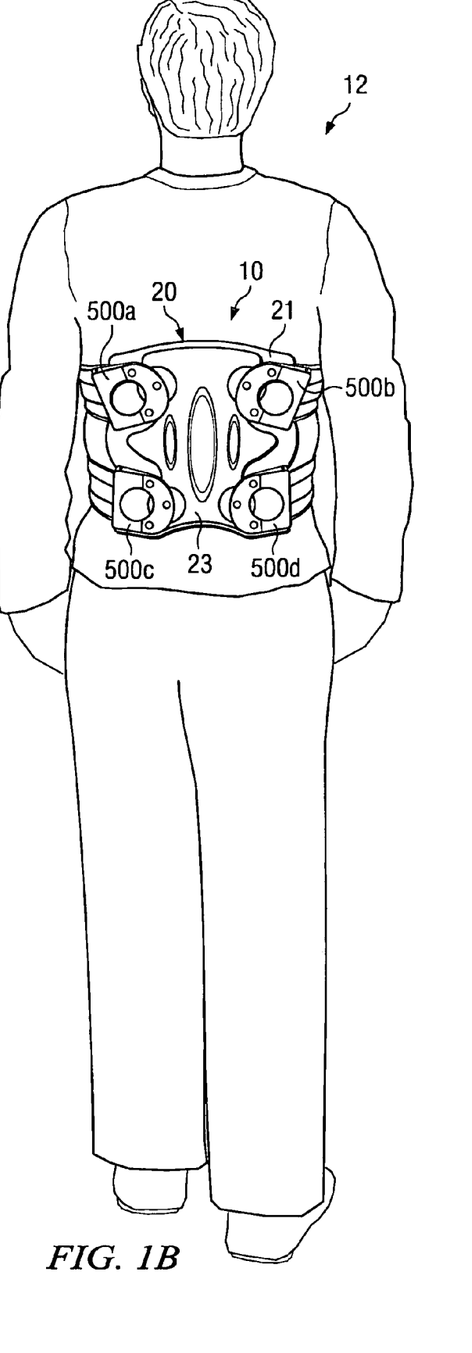

FIGS. 1A and 1B are front and rear views, respectively, illustrating a user 12 wearing an example stabilization brace 10. In the illustrated embodiment, stabilization brace 10 is operable to control the range of motion of the user's spine, limiting the degree of flexion to a predetermined range. However, in other embodiments, stabilization brace 10 may be modified to control the range of motion and limit the degree of flexion of any joint, such as the knee, elbow, or neck.

Stabilization brace 10 includes an upper belt 14 and a lower belt 16. Belts 14, 16 may be formed in any suitable manner that allows them to be positioned around a desired portion of the user's body. Example details of one embodiment of belts 14, 16 are described in greater detail below with reference to FIG. 4. In the illustrated embodiment, stabilization brace 10 also includes one or more supports 400, a backplate 20, a pair of canting mechanisms 500 associated with each support belt 14, 16, and a pair of locking mechanisms 22a, 22b associated with each support belt 14, 16.

Backplate 20, as illustrated in FIG. 1B, generally conforms to the lower back of user 12. Hence, backplate 20 may have any suitable shape and may be formed from any suitable material. In the illustrated embodiment, backplate 20 includes a foam portion 21 and a rigid portion 23. Foam portion 21 may have any suitable thickness, and functions to provide comfort to user 12 when user 12 is wearing stabilization brace 10. Rigid portion 23, which may be formed from any suitable material, functions to provide support to the lower back of user 12 and, as described in further detail below, to support canting mechanisms 500 that couple to ends of belts 14, 16. Foam portion 21 and rigid portion 23 may be coupled together in any suitable manner, such as through adhesive coupling, mechanical coupling, or any other suitable joining process. Backplate 20 may incorporate an integrated pneumatic or other fluidic lumbar pad to provide increased comfort and lumbar support.

Figure 2A:
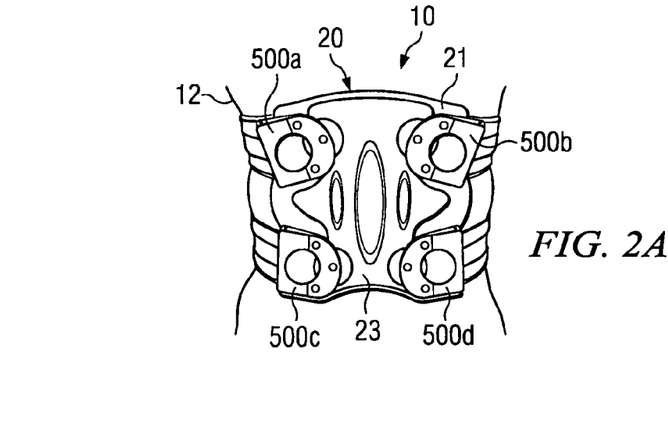
FIGS. 2A and 2B illustrate examples in which canting mechanisms allow corresponding belts to conform to the underlying structure and natural conical shapes of a particular user's body.
Figure 2B:
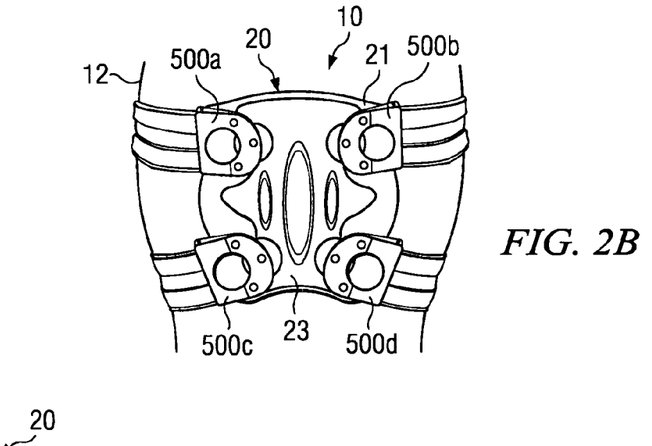

Canting mechanisms 500 are described in greater detail below with reference to FIGS. 6A and 6B. Generally, canting mechanisms 500 couple corresponding portions of belts 14, 16 to backplate 20 and ensure that belts 14, 16 conform to the user's body in a correct and comfortable manner. For example, as shown in FIGS. 2A and 2B, canting mechanisms 500 preferably allow belts 14, 16 to conform to the underlying structure and natural conical shapes of the particular user's upper torso generally below the ribs (upper belt 14) and lower torso generally above the hips (lower belt 16). FIG. 2A illustrates belts 14, 16 conformed to a user 12 having a relatively thin mid-section, while FIG. 2B illustrates belts 14, 16 conformed to a user 12 having a relatively thick mid-section, canting mechanisms 500 providing for a correct and comfortable fit in either situation. Details regarding one method of fitting stabilization brace 10 to user 12 using canting mechanisms 500 is described below with reference to FIG. 7.

Referring again to FIG. 1, to secure upper belt 14 and lower belt 16 around the user's body, locking mechanisms 22a and 22b, respectively, are utilized. As described in greater detail below with reference to FIG. 4, in one embodiment each locking mechanism 22 includes a notched strap 30 having a number of notches and a latch 32 for securing locking mechanism 22 in place in a desired notched location after the corresponding belt 14, 16 has been positioned around the user's body. Locking mechanisms 22 may be replaced with any suitable mechanism for securing belts 14, 16 in a desired location, such as snaps, hook and loop type fasteners, or other suitable mechanisms.

As described in greater detail below with reference to FIG. 5, in one embodiment supports 400 each include a motion limiter 408 that controls the range of motion of the user's spine, limiting the degree of flexion to a predetermined, preferably adjustable, range based on the location of motion limiter 408. Supports 400 may also each include one or more elastic members 406 that provide a predetermined, preferably adjustable, level of resistance against flexion of the user's spine based on the elasticity and number of elastic members 406 used. Coupling of supports 400 to belts 14, 16 may be accomplished in any suitable manner, such as through adhesive coupling, mechanical coupling, or any other suitable technique. Example locations of supports 400 about the circumference of belts 14, 16 are further illustrated in FIG. 3.

In operation, in one embodiment, user 12 is fitted for stabilization brace 10 as described below in conjunction with FIG. 7. After being properly fitted for stabilization brace 10, user 12 positions stabilization brace 10 around the user's torso, adjusts belts 14, 16 to a desired tension, and allows belts 14, 16 to conform to the user's underlying structure and natural conical shapes using canting mechanisms 500. User 12 may then secure belts 14, 16 in place using locking mechanisms 22. Because supports 400 are positioned near the abdomen of user 12, supports 400 are able to control the motion of the user's spine, limiting the degree of flexion to a predetermined range and preferably also providing a predetermined level of resistance against such flexion. Depending on the location of motion limiter 408 (FIG. 5) and the elasticity of elastic member 406 (FIG. 5), user 12 is prevented from bending forward too far, encounters resistance while bending forward, or preferably both. As described in greater detail below, the maximum degree of flexion may be adjustable, the amount of resistance encountered may be adjustable, or both. Stabilization brace 10 may be ambulatory, being portable and wearable during everyday activities. As such, stabilization brace 10 may be applied at home, at work, at play, or during travel at the convenience of user 12. Therefore, user 12 may be more likely to comply with rehabilitation guidelines than if user 12 is required to travel to a clinic for rehabilitation.

Figure 3:
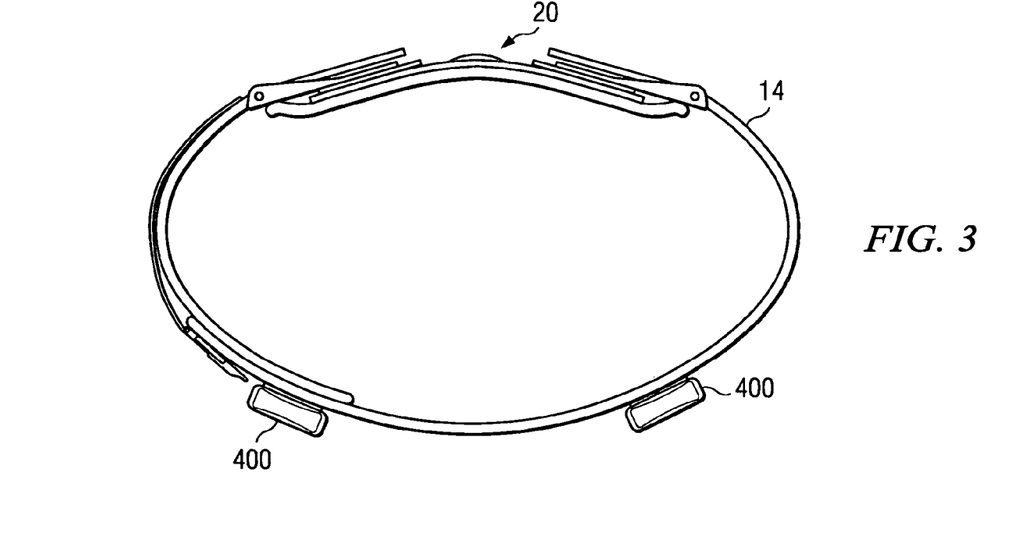
FIG. 3 is a top plan view illustrating an example stabilization brace showing example locations for supports for limiting a user's degree of flexion to a predetermined range.

FIG. 3 is a top plan view illustrating an example stabilization brace 10 showing example locations for supports 400. In FIG. 3, two supports 400 are shown in a location that generally corresponds to the front of the user's body near the abdomen. However, there may be any suitable number of supports 400 and they may be located at any suitable locations around the circumference of belts 14, 16. For example, if side-to-side flexion of user 12 is a concern, then supports 400 may be located towards the sides of belts 14, 16.

Figure 4:
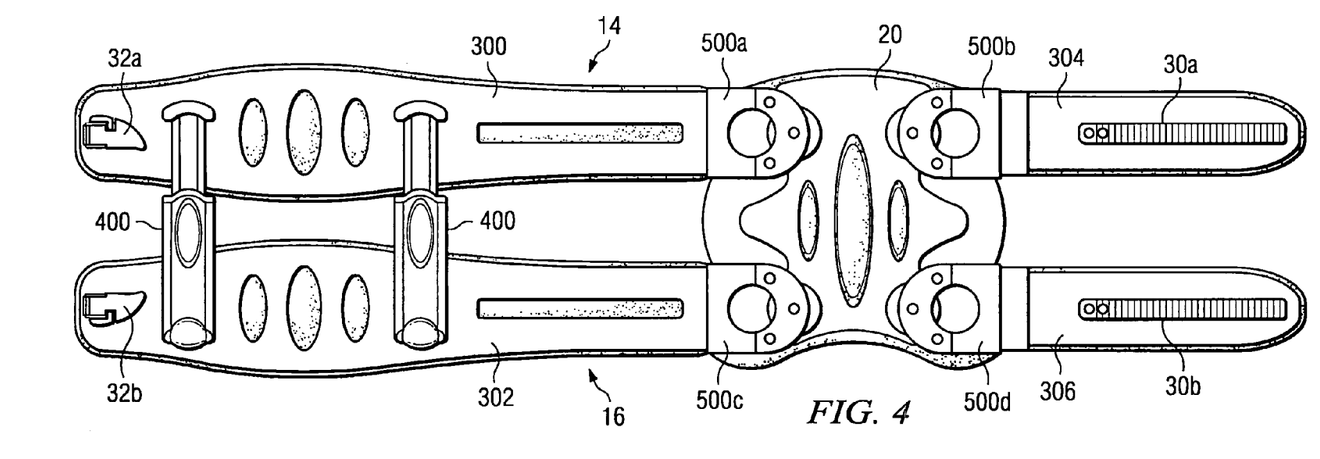
FIG. 4 is a schematic view illustrating example upper and lower belts of a stabilization brace.

FIG. 4 is a schematic view illustrating example upper belt 14 and lower belt 16. As illustrated in FIG. 4, in one embodiment, upper belt 14 includes an upper main belt 300 and an upper secondary belt 304. Similarly, lower belt 16 includes a lower main belt 302 and a lower secondary belt 306. All portions of belts 14, 16 may be formed from any suitable material. In the illustrated embodiment, all portions of belts 14, 16 include foam, woven, or other resilient portions and plastic or other rigid portions similar to backplate 20. The resilient portions and rigid portions may be coupled together in any manner, such as through adhesive or mechanical coupling. The resilient portions and rigid portions may also have any suitable size and shape. In addition, the spacing of upper belt 14 from lower belt 16 may be any spacing suitable for the size and shape of user 12.

In one embodiment, upper main belt 300 is coupled to an upper portion of backplate 20 by canting mechanism 500*a* at one end and includes latch 32*a* of locking mechanism 22*a* at the other end. Upper secondary belt 304 is coupled to the upper portion of backplate 20 opposite upper main belt 300 by canting mechanism 500*b*. Upper secondary belt 304 also includes notched strap 30*a* of locking mechanism 22*a*. As a result, when stabilization brace 10 is positioned around user 12, notched strap 30*a* and latch 32*a* will preferably coincide with one another at a particular location around the circumference of the user's body. The lengths of upper main belt 300 and upper secondary belt 304 may be determined during the fitting of stabilization brace 10 for a particular user 12. One embodiment of this fitting is described in greater detail below with reference to FIG. 7. The coupling of upper main belt 300 and upper secondary belt 304 to backplate 20 by canting mechanisms 500*a*, 500*b* is described in further detail below with reference to FIGS. 6A and 6B.

In one embodiment, lower main belt 302, similar to upper main belt 300, includes latch 32*b* of locking mechanism 22*b* at one end and is coupled to a lower portion of backplate 20 at the other end by canting mechanism 500*c*. Lower secondary belt 306, similar to upper secondary belt 304, includes notched strap 30*b* at one end and is coupled opposite lower main belt 302 to the lower portion of backplate 20 at the other end by canting mechanism 500*d*. The lengths of lower main belt 302 and lower secondary belt 306 may be determined during the fitting of stabilization brace 10 for a particular user 12, as for upper main belt 300 and upper secondary belt 304.

Also shown in FIG. 4 are supports 400 coupled between upper main belt 300 and lower main belt 302. Again, supports 400 may be coupled to upper main belt 300 and lower main belt 302 in any suitable manner.

Figure 5:
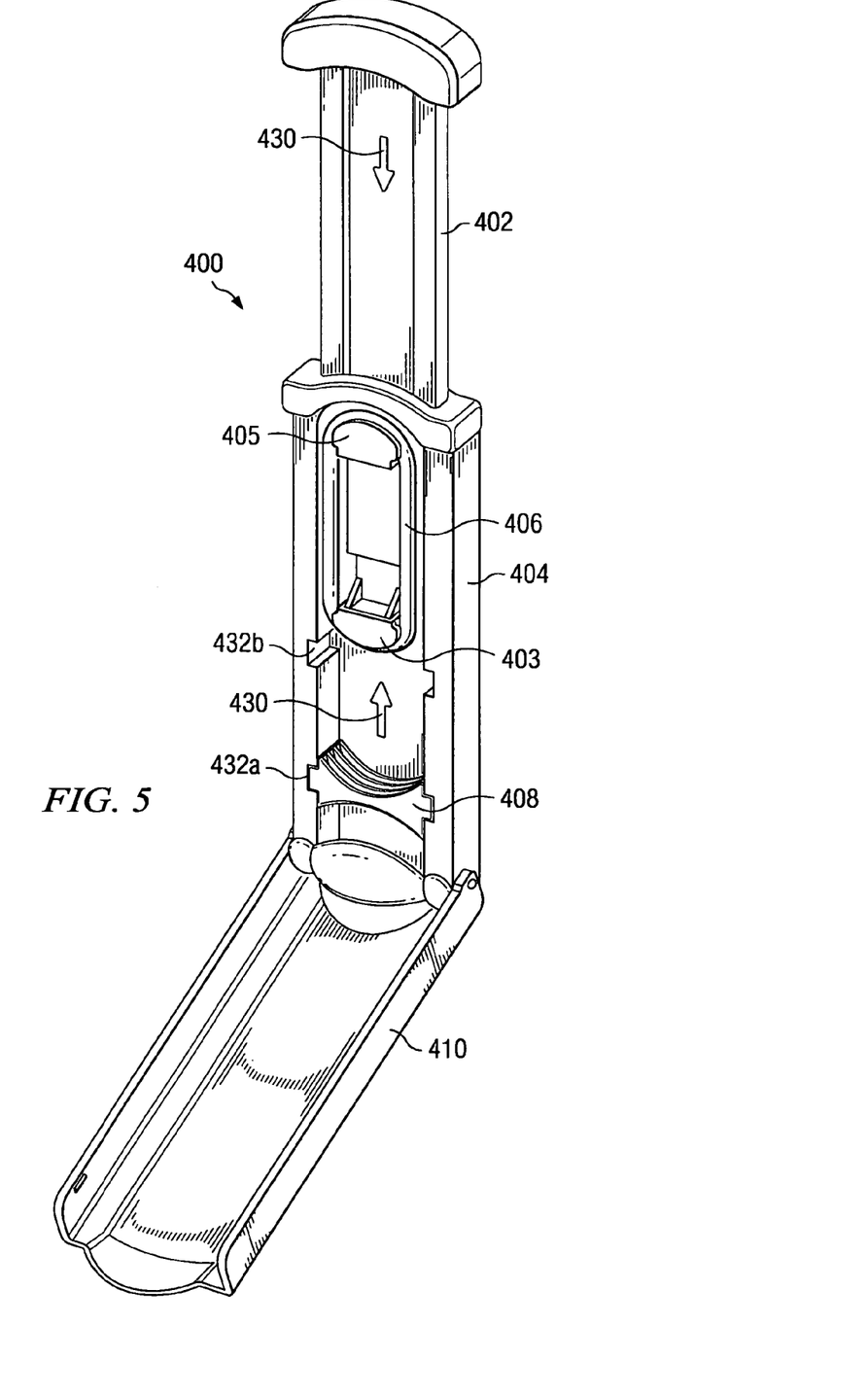
FIG. 5 illustrates an example support for limiting a user's degree of flexion to a predetermined range.

FIG. 5 illustrates an example support 400. Other suitable supports may be utilized in other embodiments. In one embodiment, support 400 includes a piston 402 having a protuberance 403, a housing 404 having a protuberance 405, an elastic member 406 coupled between protuberance 403 and protuberance 405, a motion limiter 408, and a piston cover 410. Support 400 is shown in a generally uncompressed state that corresponds to a generally upright position of user 12. As user 12 bends forward, piston 402 and housing 404 move in the directions of arrows 430. This movement forces elastic member 406 to elongate, which provides a force resisting user 12 from bending forward. The amount of this resistance depends on the elasticity and number of elastic members 406 used. Piston 402 may eventually reach a stopping point, which is dictated by the position of motion limiter 408.

Piston 402 and housing 404 may have any suitable size and shape and may be formed from any suitable material, although support 400 preferably maintains a low profile against the user's body for comfort, wearability, and aesthetic purposes. Piston 402 may be coupled to upper belt 14 in any suitable manner and housing 404 may be coupled to lower belt 16 in any suitable manner. Protuberance 403 may be formed integral with piston 402 or may be a separate element coupled to piston 402 in any suitable manner. Similarly, protuberance 405 may be formed integral with piston housing 404 or may be a separate element coupled to piston housing 404 in any suitable manner. Although protuberances 403 and 405 may have any suitable shape, they are configured to provide secure engagement with elastic member 406. The distance between protuberances 403 and 405 when support 400 is in a generally uncompressed state may be any suitable distance.

Elastic member 406 may be an elastomer formed from any suitable elastomeric material. Elastic member 406, as illustrated in FIG. 5, fits around protuberance 403 at one end and around protuberance 405 at the other end. Elastic member 406 should preferably conform to its natural shape when installed around protuberances 403 and 405 such that there is no slack therein which would effect the resistance that user 12 feels when bending forward. Elastic member 406 may be interchangeable with other elastic members 406 having different elasticities, as a result of their thicknesses or the inherent elasticities of the elastomeric materials from which they are formed, to control the amount of resistance encountered. There may be more than one elastic member 406 simultaneously disposed around protuberances 403 and 405. In an embodiment where multiple elastic members 406 may be utilized simultaneously, one or more elastic member 406 may be selectively installed or removed to increase or decrease, respectively, the amount of resistance encountered.

Motion limiter 408 may be formed from any suitable material and may couple to housing 404 in any suitable manner. In one embodiment, motion limiter 408 removably couples to housing 404 using a pair of motion limiter grooves 432*a*. The position of motion limiter 408 is adjustable with respect to housing 404 depending on the desired stopping position for piston 402. For example, motion limiter 408 may be removably coupled to housing 404 at a pair of motion limiter grooves 432*b* that corresponds to zero travel for piston 402 or motion limiter 408 may be removably coupled to housing 404 using motion limiter grooves 432*a* (as illustrated) that allow for some predetermined travel for piston 402. In a particular embodiment, motion limiter 408 may be removed completely such that the bottom of housing 404 is used as a stop. Grooves 432 may be formed in piston housing 404 at any suitable location and there may be any suitable number of grooves formed therein.

Cover 410 may be coupled to housing 404 in any suitable manner; however, in one embodiment, cover 410 is hinged to housing 404. Cover 410 facilitates access to the inside of housing 404 so that elastic member 406 may be readily removed and/or replaced and so that motion limiter 408 may be moved and/or removed. As described above, any number of supports 400 may be used around the circumference of stabilization brace 10 to control the degree of flexion of the user's spine in any number of directions.

Figure 6A:
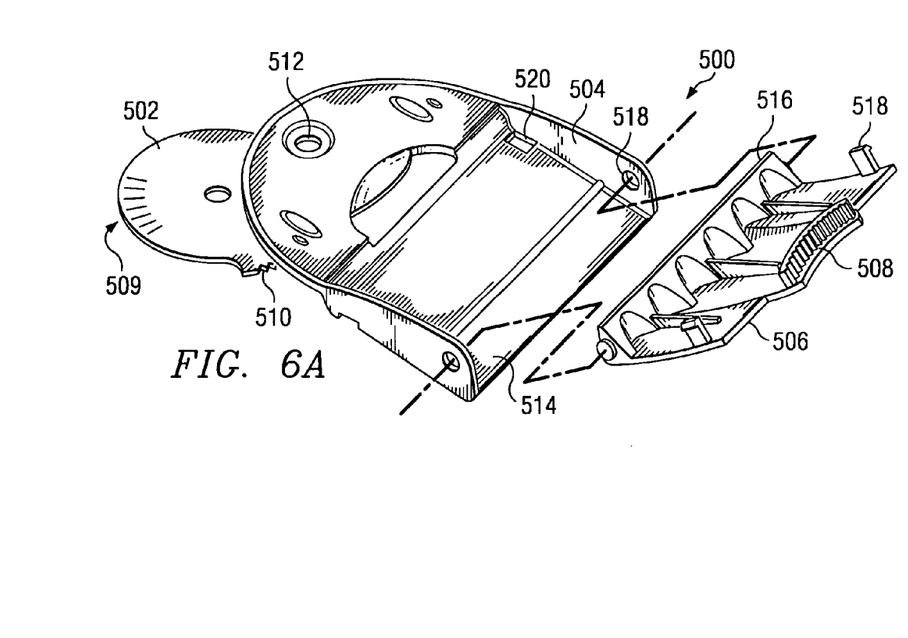
FIG. 6A illustrates an example canting mechanism.

FIG. 6A illustrates an example canting mechanism 500. As described above, canting mechanisms 500 couple ends of belts 14, 16 to backplate 20 and help ensure that belts 14, 16 conform to the underlying structure and natural conical shapes of the user's body to provide a correct and comfortable fit. Accordingly, in one embodiment, a portion of each belt 14, 16 is secured within a buckle base 504 with a buckle lever 506, which is shown in FIG. 6A to be hingedly coupled to buckle base 504 at a pivot 518. Buckle base 504 may have any suitable shape and may be formed from any suitable material. Buckle base 504 includes a receptacle 514 to accept an end of belt 14, 16. Buckle base 504 also includes a pair of notches 520 formed therein to accept a pair of latches 518 on buckle lever 506 so that buckle lever 506 may be securedly engaged with buckle base 504 to hold the end of belt 14, 16 within receptacle 514. Buckle lever 506 functions to secure the end of belt 14, 16 within receptacle 514 with a protrusion 516 near one of its ends. Buckle lever 506 may have any suitable shape and may be formed from any suitable material.

In the illustrated embodiment, buckle base 504 is rotatably coupled to backplate 20 at pivot 512 in a suitable manner, such as through mechanical coupling. This rotatable coupling allows belt 14, 16 to rotate about pivot 512 to conform to the user's body. Once the desired degree of cant is achieved, then buckle lever 506 is closed to secure belt 14, 16 within receptacle 514 of buckle base 504. The closure of buckle lever 506 prevents canting mechanism 500 from rotating once the desired degree of cant is achieved. This is accomplished with the help of a buckle locking disc 502.

Buckle locking disc 502 may be coupled to backplate 20 in any suitable manner. In addition, buckle locking disc 502 may be rotatably coupled to buckle base 504 at pivot 512. Buckle locking disc 502, which may have any suitable shape and may be formed from any suitable material, may include one or more canting indicators 509 that function to indicate the degree of cant to a person that is fitting stabilization brace 10 for user 12. Once the desired degree of cant is achieved, buckle base 504 and buckle lever 506 may be prevented from rotating by engaging buckle lever 506 with buckle locking disc 502. Buckle locking disc 502 includes a set of gear teeth 510 that mesh with a set of gear teeth 508 on buckle lever 506 when buckle lever 506 is in a closed position. This meshing of gear teeth 508 and gear teeth 510 locks buckle base 504 in place so that buckle base 504 is unable to rotate with respect to backplate 20. This meshing is illustrated in FIG. 6B, which is a view of canting mechanism 500 from the back side.

Figure 6B:
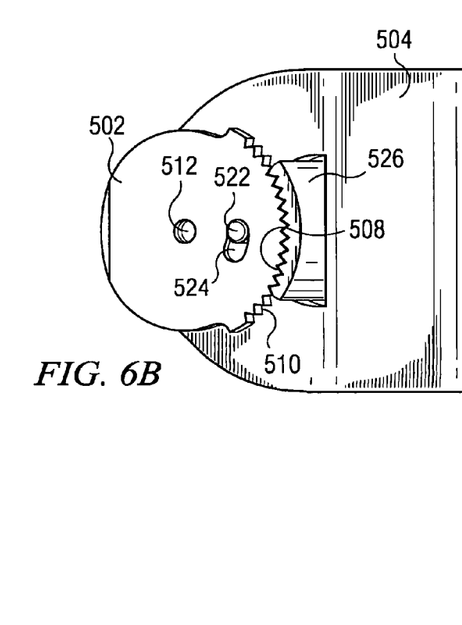
FIG. 6B is a perspective view of the example canting mechanism of FIG. 6A illustrating the interaction between an example buckle locking disc and an example buckle base of the canting mechanism.

Referring to FIG. 6B, the set of gear teeth 508 on buckle lever 506 is shown meshed with the set of gear teeth 510 on buckle locking disc 502. The meshing may be facilitated by an opening 526 formed in buckle base 504. Also shown is a protuberance 522 coupled to the underside of buckle base 504 that engages a slot 524 formed in buckle locking disc 502. The length of slot 524 determines how much rotation of buckle base 504 is allowed before buckle base 504 is prevented from rotating by the meshing of gear teeth 508 and gear teeth 510.

Figure 7:
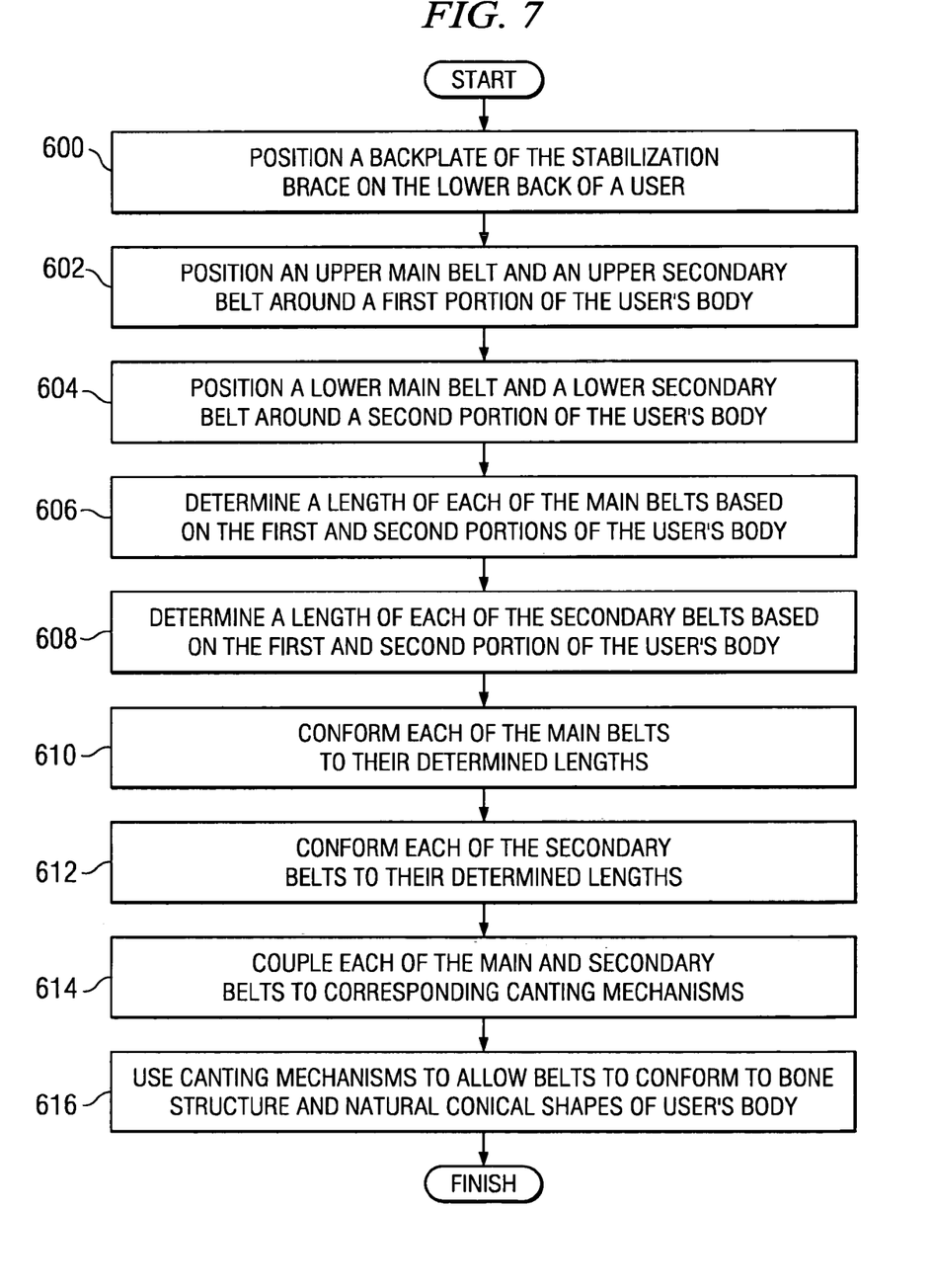
FIG. 7 illustrates an example method for fitting a user for a stabilization brace.

FIG. 7 illustrates an example method for fitting user 12 for stabilization brace 10. Upper belt 14 and lower belt 16 of stabilization brace 10 may be fitted concurrently in some embodiments or consecutively in other embodiments. The example method begins at step 600 where backplate 20 of stabilization brace 10 is positioned on the lower back of user 12. Backplate 20 includes a first pair of canting mechanisms 500 coupled to a first side of backplate 20 and a second pair of canting mechanisms 500 coupled to a second side of backplate 20. Upper main belt 300 and upper secondary belt 304 are positioned around a first portion of user 12 at step 602. Lower main belt 302 and lower secondary belt 306 are positioned around a second portion of user 12 at step 604.

In one embodiment, belts 14, 16 are provided with lengths that can accommodate the largest typical user 12. For smaller users 12, portions of belts 14, 16 may be reduced in length to fit the particular user 12. Therefore, the proper lengths of belts 14, 16 need to be determined. Accordingly, at step 606, the lengths of upper main belt 300 and lower main belt 302 are determined based on the first and second portions of the user's body, respectively. For example, the first portion of the body may be the upper torso below the ribs and the second portion of the body may be the lower torso above the hips. The lengths of upper secondary belt 304 and lower secondary belt 306 may also be determined based on the first and second portions of the body, at step 608. Once the proper lengths are determined, upper main belt 300 and lower main belt 302 may be conformed to their determined lengths at step 610 and if applicable, upper secondary belt 304 and lower secondary belt 306 may be conformed to their determined lengths at step 612. In certain embodiments, this conforming may include cutting excess length of a particular belt portion. In some embodiments, not all belt portions will have to be conformed to their determined lengths because one or more belt portions may have the proper length for a particular user 12.

At step 614, upper main belt 300, lower main belt 302, upper secondary belt 304, and lower secondary belt 306 are coupled to backplate 20 using corresponding canting mechanisms 500. This may include placing an end of each of the main and secondary belts in receptacle 514 of a corresponding buckle base 504 and clamping down on the end with buckle lever 506 that is hingedly coupled to buckle base 504. Before clamping down on the end, however, at step 616 each canting mechanism 500 may be allowed to rotate about associated pivot 512 to allow its corresponding belt portion to adjust to conform to the underlying structure and natural conical shapes of the user's body. Then buckle lever 506 may be closed to secure canting mechanism 500 in its correct position. This ends the example method outlined in FIG. 7.

Figure 8:
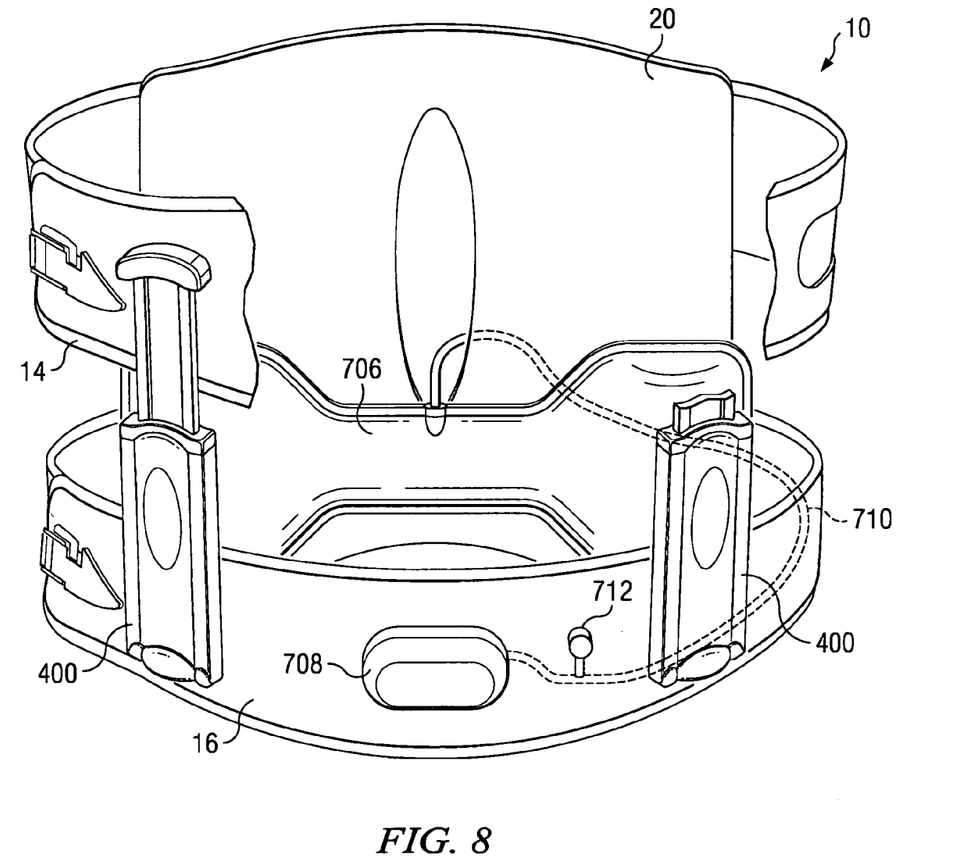
FIG. 8 is a front view illustrating an example stabilization brace with an integrated lumbar support system.

FIG. 8 is a front view illustrating an example stabilization brace 10 with an integrated lumbar support system. Although stabilization brace 10 is illustrated and described by way of example, the present invention contemplates the lumbar support system being incorporated into any suitable stabilization, traction, or other brace, for example, a brace providing spinal traction as illustrated and described in U.S. Pat. No. 6,533,740 B2. Furthermore, although stabilization brace 10 with belts 14, 16 is illustrated and described by way of example, the present invention contemplates the lumbar support system being incorporated into a brace having one, two, or any other number of belts.

In one embodiment, as described above, belts 14, 16 may each include one or more plastic or other rigid portions, which may be arranged as one or more sheets having substantially the same width as belts 14, 16, arranged as one or more strips substantially thinner than belts 14, 16, or arranged in any other suitable manner with respect to belts 14, 16. Belts 14, 16 may also include one or more foam, woven, or other resilient portions coupled to the one or more rigid portions as appropriate. In one embodiment, each belt 14, 16 includes a rigid portion, located on an outward-facing surface of belt 14, 16 along substantially the entire length of belt 14, 16, and a resilient portion, which underlies the rigid portion where the rigid portion is present but is exposed otherwise. However, as described above, belts 14, 16 may have any suitable constructions according to particular needs.

In one embodiment, the lumbar support system integrated with stabilization brace 10 includes a pneumatically inflatable lumbar pad 706, a pump 708, a pump tube 710, and a release valve 712. A portion of pump 708 may be located within the material of lower belt 16 such that pump 708 is considered at least partially integrated within lower belt 16. For example, a base or other portion of pump 708 may be secured or otherwise located between the rigid portion and the underlying resilient portion of lower belt 16. Similarly, a portion of pump tube 710 may be located within lower belt 16 such that pump tube 710 is considered at least partially integrated within lower belt 16. For example, a portion of tube 710 may be secured or otherwise located between the rigid portion and the underlying resilient portion of lower belt 16. Where the brace incorporating the integrated lumbar support system has only a single belt about the user's lower torso, pump 708 and pump tube 710 may be at least partially integrated within the single belt. A fitting may be used to couple together opposing portions of pump tube 710, as described more fully below with reference to FIGS. 9 and 10.

Lumbar pad 706 is coupled to backplate 20 and provides lumbar support to a user of stabilization brace 10. In one embodiment, lumbar pad 706 may be coupled to a foam portion of backplate 20. Lumbar pad 706 may be coupled to backplate 20 using any suitable fixed or adjustable fasteners, such as Velcro for example. The use of Velcro or other adjustable fasteners may allow the user to readily reposition lumbar pad 706 with respect to backplate 20 as desired to provide increased lumbar support and comfort.

Pump 708 may be used by a user of stabilization brace 10 to inflate lumbar pad 706. Pump tube 710 couples pump 708 to lumbar pad 706 to transport air to lumbar pad 706 for inflation. A user may repeatedly press or squeeze pump 708 in order to inflate lumbar pad 706. Release valve 712 is also coupled to pump tube 710. When a user desires to partially or substantially deflate lumbar pad 706, when removing stabilization brace 10 for example, the user may press release valve 712 which releases air from lumbar pad 706 through pump tube 710.

Figure 9:
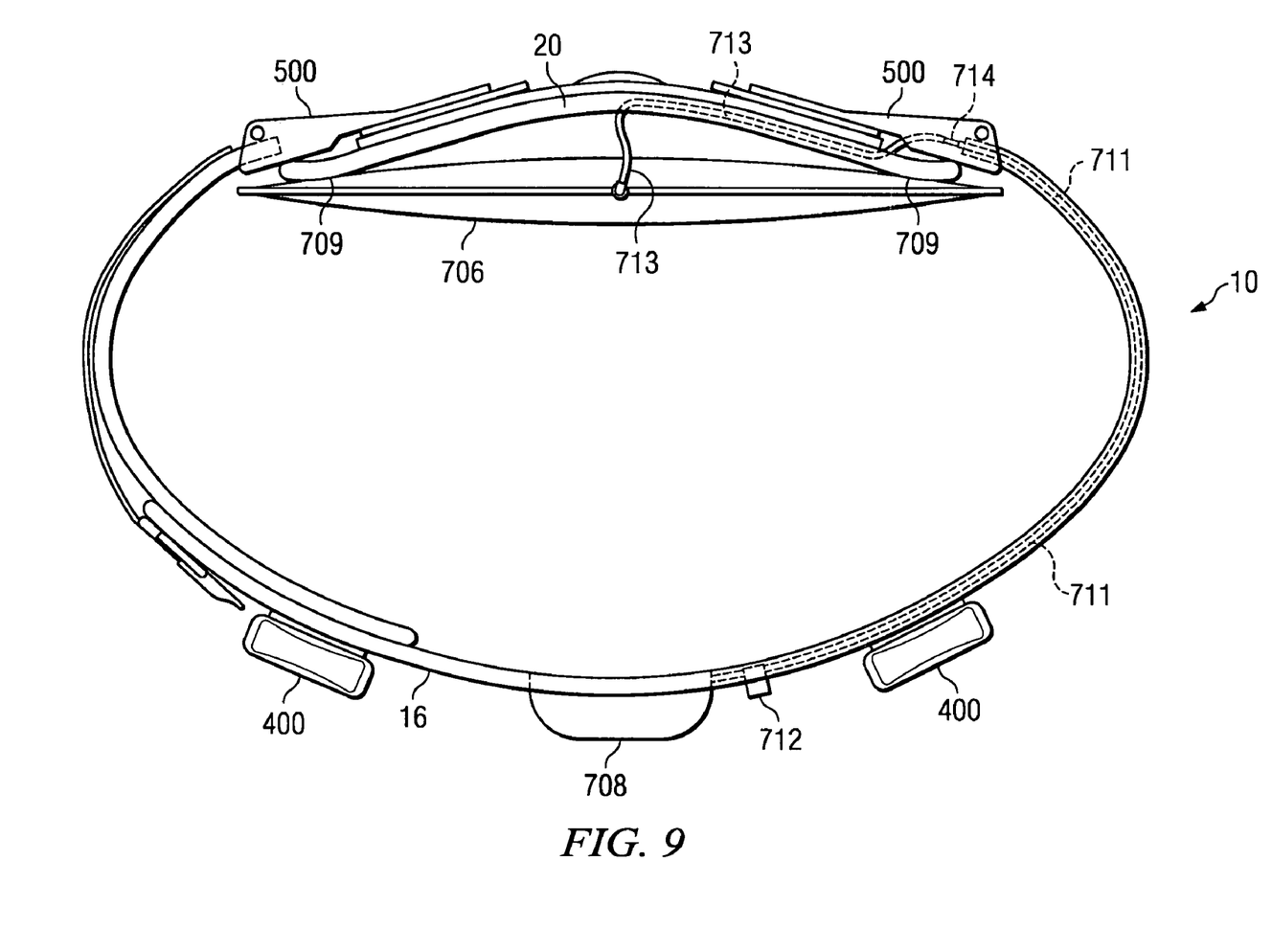
FIG. 9 is a top plan view illustrating the example stabilization brace of FIG. 8.

FIG. 9 is a top plan view illustrating example stabilization brace 10 of FIG. 8. In the illustrated embodiment, lumbar pad 706 is coupled to backplate 20 in two locations using Velcro or other suitable fasteners 709. However, lumbar pad 706 may be coupled to backplate 20 at any number of locations according to the shapes of lumbar pad 706 and backplate 20 and any other suitable considerations. As described above, a portion of pump tube 710 may be at least partially integrated within lower belt 16. In the illustrated embodiment, pump tube 710 includes a first portion 711 and a second portion 713. First portion 711 of pump tube 710 is coupled to pump 708 and to release valve 712 and is at least partially integrated within lower belt 16. In a more particular embodiment, first portion 711 of pump tube 710 is secured between the rigid and resilient portions of lower belt 16 along the entire length of first portion 711 or a substantial portion thereof. Second portion 713 of pump tube 710 is coupled to lumbar pad 706 and may be at least partially integrated within backplate 20. For example, second portion 713 of pump tube 710 may be secured or otherwise located between foam portion 21 and rigid portion 23 of backplate 20 along part of the length of second portion 713. First portion 711 and second portion 713 may be coupled together using a hollow fitting 714. The ends of first portion 711 and second portion 713 force fit over the opposing ends of fitting 714 to couple first portion 711 to second portion 713. Other embodiments may utilize other components or methods to couple together portions of pump tube 710.

As described above with respect to the example method of FIG. 7, upper and lower belts 14, 16 may be fit to a particular user by cutting off an excess length of each belt 14, 16. When the illustrated stabilization brace 10 is manufactured, lower belt 16 may include an excess portion which must be cut off to cut lower belt 16 to length to fit a particular user. Where first portion 711 of pump tube 710 is integrated within lower belt 16, the excess portion of lower belt 16 that must be cut off may also include an excess portion of first portion 711 of pump tube 710. Thus, the cutting of lower belt 16 to length to fit a particular user may also substantially simultaneously involve the cutting of first portion 711 of pump tube 710 to the same length. In one embodiment, the integration of first portion 711 of pump tube 710 into lower belt 16 allows first portion 711 to remain protected within lower belt 16 during fitting and use such that it is less likely to become dislodged, to cause discomfort to the user, or to hinder the operation of the lumbar support system, yet still allows first portion 711 of pump tube 710 to be easily cut to the appropriate length during fitting for coupling to second portion 713 of pump tube 710. As a result, the lumbar support system may provide improved performance, comfort, and attractiveness as compared to a lumbar support system in which a tube between a pump and a lumbar pad is not integrated within a belt of an associated brace.

Figure 10:
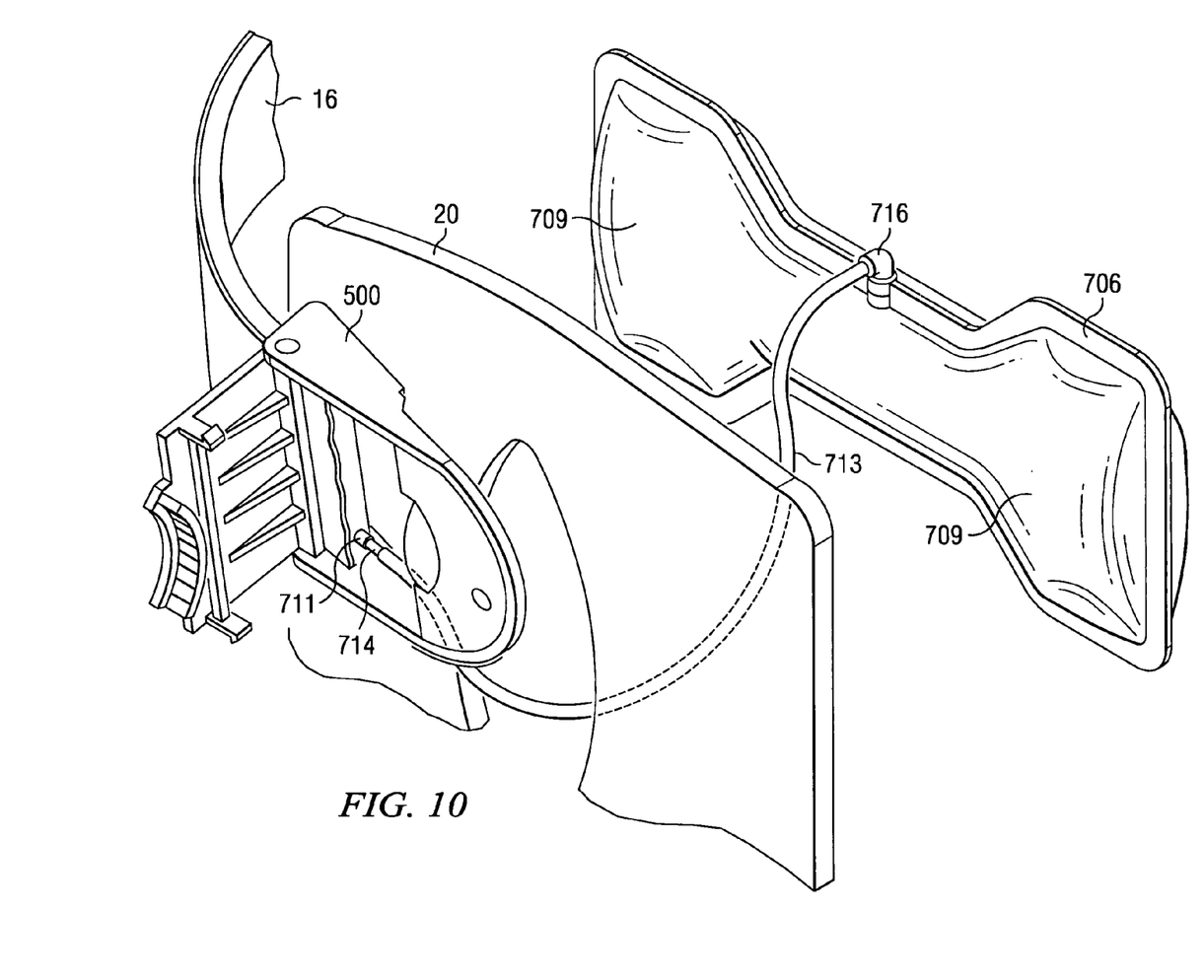
FIG. 10 is a perspective view illustrating portions of an example integrated lumbar support system.

FIG. 10 is a perspective view illustrating portions of an example integrated lumbar support system. In the illustrated embodiment, first portion 711 of pump tube 710 couples to second portion 713 of pump tube 710 using fitting 714 proximate a canting mechanism 500. First portion 711, as described above, may be cut to a desired length as upper belt 16 is cut to fit the user. Second portion 713 of pump tube 710 couples to lumbar pad 706 to transport air to and from lumbar pad 706 for inflation and deflation of lumbar pad 706 as desired. The coupling of second portion 713 to lumbar pad 706 may be accomplished in any suitable manner, such as using an elbow fitting 716 as illustrated.

Although the present invention is described with several embodiments, numerous changes, substitutions, variations, alterations, and modifications may be suggested to one skilled in the art, in the intention is that the invention encompass all such changes, substitutions, variations, alterations, and modifications as falls within the spirit and scope of the appended claims.

What is claimed is:

1. A brace with an integrated lumbar support system, comprising:

an upper belt adapted to be positioned about a user's upper torso, the upper belt comprising a rigid portion and a resilient portion each extending along at least a portion of a length of the upper belt;

a lower belt adapted to be positioned about the user's lower torso, the lower belt comprising a rigid portion and a resilient portion each extending along a length of the lower belt;

a lumbar pad coupled to the lower belt, the lumbar pad adapted to be positioned proximate the user's lumbar region and to be inflated to provide lumbar support to the user;

a pump coupled to the lower belt, the pump adapted to provide air to the lumbar pad to inflate the lumbar pad;

a tube adapted to transport air between the pump and the lumbar pad to inflate the lumbar pad, the tube comprising:

a hollow fitting coupling a first tube portion and a second tube portion;

the first tube portion coupled between the pump and the coupling, the first tube portion secured between the rigid portion and the resilient portion of the lower belt along substantially the entire length of the lower belt between the pump and the coupling to integrate the first tube portion within the lower belt, an end of the first tube portion being force fitted over a first end of the coupling, the first tube portion adapted to be cut to length substantially simultaneously with the lower belt being cut to length to be positioned about the user's lower torso; and the second tube portion coupled between the lumbar pad and the coupling, an end of the second tube portion being force fitted over a second end of the coupling.

2. The brace of claim 1, further comprising a release valve coupled to the tube, the release valve adapted to release air from the lumbar pad through the tube in response to depression of the valve.

3. The brace of claim 1, further comprising a backplate coupled to the belt and supporting the lumbar pad.

4. The brace of claim 3, wherein the backplate is pivotally coupled to the belt to allow rotation of the belt about the backplate.

5. The brace of claim 1, further comprising one or more supports coupled between the upper and lower belts, each support comprising:

a housing;

a piston slidably engaged with the housing; and a motion limiter adjustably coupled to the housing in one of a plurality of predetermined positions, the support operable to limit flexion of the user's spine to a predetermined range according to the position of the motion limiter.

* * * * *